United States Patent [19]

Babbs et al.

[11] Patent Number: 4,978,668

[45] Date of Patent: Dec. 18, 1990

[54] TREATMENT TO REDUCE ISCHEMIC TISSUE INJURY

[75] Inventors: Charles F. Babbs; Stephen F. Badylak, both of West Lafayette, Ind.

[73] Assignee: Purdue Research Foundation, West Lafayette, Ind.

[21] Appl. No.: 902,703

[22] Filed: Sep. 2, 1986

[51] Int. Cl.$^5$ ............................................ A61K 31/505
[52] U.S. Cl. .................................................. 514/258
[58] Field of Search ............................. 514/258, 528

[56] References Cited

U.S. PATENT DOCUMENTS

| | | | |
|---|---|---|---|
| 3,624,205 | 11/1971 | Hitchings | 514/258 |
| 3,626,064 | 12/1971 | Hitchings | 514/258 |
| 3,629,410 | 12/1971 | Heifter et al. | 514/114 |
| 3,740,433 | 6/1973 | Clody et al. | 514/263 |
| 4,656,034 | 4/1987 | Sarnoff | 514/114 |
| 4,661,469 | 4/1987 | Sarnoff | 424/166 |

OTHER PUBLICATIONS

Chem. Abst. 97:465h (1982)-Hansson et al.
Chem. Abst. 104:141978(c) (1986)-Bayati et al.
Chem. Abst. 104:161935(q) (1986)-Nordstroem et al.
Chem. Abst. 106: 194.199(m) (1987)-Grum et al.
Chem. Abst. 106: 188.759(p) (1987)-Lee et al.
Chem. Abst. 106: 188708(w) (1987)-Godin et al.
Michael J. Im, Wen-Hui Shen, et al., "Effect of Allopurinol on The Survival of Hyperemic Island Skin Flaps", Div. Plastic Surgery, Dept. Surgery, Johns Hopkins University School of Medicine, Jan. 31, 1983, pp. 276-278.
Kent A. Vasko, Richard A. DeWall, Ann M. Riley, "Effect of Allopurinol in Renal Ischemia", Surgery, May 1972, vol. 71, No. 5, pp. 787-790.
Billy Hammond, Michael Hess, "The Oxygen Free Radical System: Potential Mediator of Myocardial Injury", JACC, vol. 8, No. 1, Jul., 1985, 215-220.
DeWall, Vasko et al., "Responses of the Ischemic Myocardium to Allopurinol", American Heart Journal, Sep., 1971, vol. 82, No. 3, pp. 362-370.
James Stewart et al., "Prevention of Free Radical-Induced Myocardial Reperfusion Injury with Allopurinol", J. Thorac. Cardiovasc. Surg., Jul., 1985, vol. 90, No. 1, pp. 68-72.
Akizuki et al., "Infarct Size Limitation by the Xanthing Oxidase Inhibitor, Allopurinol, in Closed-Chest Dogs with Small Infarcts", Cardiovascular Research, 1985, 19, 686-692.
Myers et al., "Involvement of Hydrogen Peroxide and Hydroxyl Radical in the 'Oxygen Paradox'. Reduction of Creatine Kinase Release by Catalase, Allopurinol or Deferoxamine, but not by Superoxide Dismutase", J. Mol. Cell Cardiol. 17, 675, 1985.
Werns et al., "Reduction of the Size of Infarction by Allopurinol in the Ischemic-Reperfused Canine Heart", Circulation, vol. 73, No. 3, Mar., 1986, pp. 518-524.
Koyama et al., "The Role of Oxygen Free Radicals in Mediating the Reperfusion Injury of Cold-Preserved Ischemic Kidneys", Transplantation, vol. 40, No. 6, 1985, pp. 590-595.
Toledo-Pereyra et al., "Effect of Allopurinol on the Preservation of Ischemic Kidneys Perfused with Plasma or Plasma Substitutes", Ann. Surg. 80, pp. 780-782, 1974.
Toledo-Pereyra, et al., "Comparative Effects of Chlorpromazine, Methylprednisolone, and Allopurinol During Small Bowell Preservation", Am. J. Surg., vol. 126, Nov., 1973, pp. 631-634.
Toledo-Pereyra, "Effective Treatment of Severely Damaged Kidneys Prior to Transplantation", Transplantation, No. 16, 1973, pp. 79-80.
Ellen Hale, "The Deadly Side of Unstable Oxyten", Jounal and Courier, May 21, 1986, West Lafayette, Indiana, D1-D3.
Kann et al., "The Development and Use of An Intravenous Preparation of Allopurinol", Am. Journal Med. Sciences, July, 1968, vol. 256, pp. 53-63.
J. McCord, "Oxygen Derived Free Radicals in Postischemic Tissue Injury" reprinted from the New England Journal of Medicine, 1985 pp. 159-162, vol. 312.

Primary Examiner—Douglas W. Robinson
Attorney, Agent, or Firm—Barnes & Thornburg

[57] ABSTRACT

Intravenous administration of allopurinol, oxypurinol or deferoxamine to a patient suffering a condition of tissue ischemia is effective to reduce damage to affected tissues. The invention has particular application for post-resuscitative treatment of victims of heart attack or stroke.

20 Claims, No Drawings

TREATMENT TO REDUCE ISCHEMIC TISSUE INJURY

This invention relates to a method of treatment of patients suffering from a condition of body tissue ischemia. The method is effective to reduce tissue damage resulting from an ischemic condition and subsequent reperfusion of ischemic tissues.

Ischemia is a condition of tissue anoxia due to a stoppage of the inflow of arterial blood to body tissue, usually as a result of arterial obstruction or heart dysfunction, the latter resulting effectively in whole body ischemia. Reperfusion is the restoration of blood flow to tissues previously rendered ischemic. Examples of tissue damage resulting from localized ischemia include the necrosis of heart tissue subsequent to coronary thrombosis, brain damage due to a stroke, and infarction of kidney or intestine following arterial thromboembolism. Examples of techniques to establish reperfusion include vascular surgery in the case of arterial occlusion, successful intracoronary streptokinase infusion for coronary thrombosis, and successful cardiac resuscitation in the case of cardiac arrest.

The technical literature reflects a significant effort in the medical research community directed to development of an understanding of the damage observed in reperfused ischemic tissues. In fact, researchers have found that significant tissue damage resulting after a period of tissue ischemia, followed by reperfusion, occurs not only during the period of circulatory arrest, but during the period of reperfusion. Indeed, a relatively large proportion of the total injury seen after 5 to 60 minute periods of circulatory arrest may actually develop during the reperfusion phase. Such tissue damage is known as reperfusion injury.

Many medical researchers have proposed that the tissue damage associated with the so-called reperfusion injury is due to an abnormally high concentration of a species identified as a superoxide anion which is rapidly produced in previously hypoxic (oxygen starved) tissue upon the restoration of oxygenated blood flow to the hypoxic tissue. Thus while oxygen is necessary to restore normal metabolism in hypoxic tissue, body chemistry during the period of hypoxia changes to favor the production of tissue damaging superoxide anions at a rate far above the rate such anions are produced during normal metabolism, and far above the rate which the body's own protective chemistry (against the effects of superoxide) can handle. In general, the superoxide is produced by the action of xanthine oxidase in the presence of oxygen upon hypoxanthine, which is first converted to xanthine and then to uric acid by the enzyme. It has been reported in the literature that xanthine oxidase inhibitors such as allopurinol and oxypurinol can be used effectively to reduce tissue damage due to reperfusion injury if such compounds are present at effective levels in the ischemic tissue at the time of reperfusion.

The present invention is directed to the use of allopurinol, oxypurinol, or deferoxamine administered intravenously to a patient suffering a condition of tissue ischemia, said treatment being initiated subsequent to occurence of that condition and at or about the time blood flow is reestablished to said tissue. Such circumstances (i.e., tissue ischemia followed by reestablishment of blood flow) occur during cardiac arrest and resuscitation, during heart attacks caused by coronary artery occlusion followed by coronary artery thrombolysis, during a stroke and subsequent thrombolysis, and during other disease processes or medical and surgical procedures in which blood supply to body tissues is temporarily interrupted.

The present invention is directed particularly to the treatment of patients experiencing unanticipated conditions of tissue ischemia, particularly those suffering from heart attacks and strokes, where there is little if any advance warning of the onset of the ischemic tissue condition. The discovery underlying the present invention is that the presence of allopurinol, oxypurinol or deferoxamine at effective concentrations in the blood at an early stage in the tissue reperfusion process is effective to minimize reperfusion injury to that tissue. Based on the experimental results forming the basis of this invention, the compounds administered in accordance with the present invention apparently diffuse from the blood stream to cells in the reperfused ischemic tissue at a rate comparable to that of oxygen. Thus, the active compositions administered in accordance with the present method diffuse into the ischemic tissue with blood borne oxygen and, therefore, are in place to inhibit formation of tissue damaging superoxide anions or to inhibit the superoxide driven, iron catalyzed Haber-Weiss reaction, the chemical pathway by which superoxide anions are believed to degrade cell protein.

In accordance with the present invention, a method is provided for treating a patient suffering a condition of tissue ischemia to reduce tissue damage occurring during reperfusion of the ischemic tissue, which method comprises administering to said patient intravenously an effective amount of a compound selected from the group consisting of allopurinol, oxypurinol and deferoxamine, administration of said composition being initiated substantially simultaneously with the restoration of blood flow to the ischemic tissue. In accordance with a preferred embodiment of this invention such treatment is administered at the same time the patient is undergoing therapy to promote reperfusion, that is, circulation of blood to the ischemic tissue. Thus treatment in accordance with this invention can be initiated, for example, by emergency technicians immediately after cardiopulmonary resuscitation or in combination with thrombolytic therapy administered to victims of coronary thrombosis. Other examples of induced reperfusion of ischemic tissues are mesenteric artery thrombolysis, renal artery thrombolysis, pulmonary artery thombolysis, surgical imbolectomy of renal, mesenteric or femoral arteries and balloon angioplasty of coronary, renal, femoral or mesenteric arteries.

Spontaneous reperfusion of ischemic tissue occurs in victims of stroke, myocardial infarction, pulmonary embolism, intestinal infarction, renal infarction and femoral artery thromoembolism. Tissue damage due to an ischemic condition and subsequent spontaneous reperfusion can be minimized in accordance with this invention by initiating treatment as soon as possible following the ischemic episode.

Intravenous administration of allopurinol, oxypurinol and deferoxamine is also effective to minimize damage in transplanted organs and other transplanted tissue.

The composition to be administered intravenously in accordance with this invention is formulated in accordance with art recognized techniques for preparation of parenteral dosage forms. Thus the active compound is dissolved in a pharmaceutically acceptable liquid carrier such as isotonic saline solution, aqueous dextrose solution, aqueous polyethelene glycol solution, or lipid emulsions. Concentration of the active compound, allopurinol, oxypurinol or deferoxamine, aqueous ethanol solution, in the intravenous composition to be administered in accordance with this invention can range from about 0.1 mg/ml to greater than about 10 mg/ml. Of course, when the concentration of active ingredient in the IV solution is higher, a lower volume of intravenously administered solution is required for any given dosage.

Both oxypurinol and allopurinol have relatively low water solubility. Their corresponding alkali metal salts, for example the sodium or potassium salts, exhibit higher water solubility and are useful for preparation of parenteral preparations to be administered according to the present method.

Effective dosage ranges for treatment with allopurinol, oxypurinol or deferoxamine in accordance with this invention range from about 10 milligrams per kilogram to about 50 milligrams of each drug, alone or in combination, per kilograms of patient weight.

The surprising effectiveness of treatment with allopurinol, oxypurinol, or deferoxamine in accordance with the present invention, after an unexpected ischemic episode, has significant clinical importance. The discovery underlying the present invention, that the described active components are effective even when administered intravenously after the ischemic episode, was the result of numerous animal tests.

A circulatory arrest model in a rat was developed to study cerebral and cardiac resuscitation. The experimental model emphasizes long term survival in populations of 20 or more animals as an indicator of the overall success of the resuscitative effort. Whole body ischemia is produced for 5 to 20 minutes by arresting the heart with a cold potassium chloride, cardioplegic solution. Following 1 to 3 minutes of CPR, minimal, standardized post-resuscitative care is provided. As the duration of ischemia is increased from 5 to 20 minutes, survival immediately following resuscitation decreases from 100% to 25%, and survival at 48 hours post ischemia decreases from 60% to 0%. When the total circulatory arrest time is 8 to 11 minutes, the possibility of immediate resuscitation is about 80% and long term survival is about 30%.

Using that animal model, allopurinol in a parenteral solution was evaluated as post resuscitative therapy. Allopurinol sodium salt was given intravenously in a dose of 25 mg/kg immediately after restoration of circulation. Survival at ten days was as follows:

| RESPONSE | CONTROLS | ALLOPURINOL TREATED |
|---|---|---|
| Alive | 6 | 14 |
| Dead | 16 | 8 |

$X^2 = 5.78$, df = 1, p < 0.05

These data demonstrate that allopurinol when administered intravenously after return of spontaneous circulation is effective to increase survival rates following cardiac arrest.

Additional studies have shown the therapeutic effectiveness of oxypurinol to prevent reperfusion injury in heart muscle tissue when administered after 60 minutes of warm ischemia. Isolated, perfused and beating rat hearts were subjected to 60 minutes of complete ischemia and anoxia. Three groups of 10 hearts each, placebo-treated (PT), deferoxamine-treated (DT) and oxypurinol-treated (TO), were subjected to 60 minutes of warm ischemia followed by 60 minutes of reperfusion with oxygenated Locke's solution. The drugs (or placebo) were administered after the ischemic period, at the beginning of reperfusion. The mean vascular resistance increased for all groups during the 60 minutes of reperfusion compared to the value just prior to ischemia (t = −1 minute), but was significantly greater in the PT group than in the drug-treated groups. Vascular resistance increased $1,148 \pm 241$ peripheral resistance units (PRU) for the PT group, $242 \pm 94$ PRU for the DT group ($t_s = 3.50$, df = 8, P < 0.01, compared to the PT group), and $183 \pm 47$ PRU for the OT group ($t_s = 3.94$, df = 8, P < 0.01, compared to the PT group). There was no significant difference between the DT and TO groups. The mean CPK release during reperfusion was also significantly greater than for either of the drug-treated groups. The total CPK release (IU/gm/60 minutes) was $1,137 \pm 311$ for the PT group, $452 \pm 209$ for the DT group ($t_s = 4.10$, df = 8, P < 0.01, compared to the PT group) and $231 \pm 200$ for the OT group ($t_s = 4.10$, df = 8, P < 0.01, compared to the PT group). There was no significant difference between the DT and OT groups. Morphometric evaluation of electron micrographs showing ultra structural changes within the same hearts showed that significantly less mitochondrial swelling occurred in the DT and OT groups (2.14 and 1.85 microns$^2$ cross-sectional diameter, respectively) vs. the PT group (2.50, P < 0.01). This study demonstrated that the isolated rat heart model was an effective model for the study of reperfusion injury and that the drugs found effective in whole rat model also proved effective in this model, even when administered after the ischemic episode.

The effectiveness of oxypurinol for enhancing heart function following an ischemic episode was also evaluated using the isolated rat heart model. Following 30 minutes of total ischemia, oxypurinol was administered in the perfusate at 200 micrograms/ml and was given at the onset of reperfusion. The results showed a dramatic improvement in the ability of the heart to produce pressure and flow when oxypurinol was administered compared with placebo treatment.

In another study designed to further evaluate the effectiveness of oxypurinol to prevent renal tissue damage, 10 rats were pre-treated with oxypurinol (25 mg/kg, IP), as might be done in the clinical setting of kidney transplantation. 10 control rats were similarly treated with saline solution. Following unilateral nephrectomy, each rat's remaining kidney was subjected to 45 minutes of warm ischemia by clamping the renal artery and vein. The clamp was then released for reperfusion and survival monitored as the endpoint of the experiment. Two additional doses of oxypurinol (25 mg/kg) or placebo were given to the respective groups, one given intravenously immediately after reperfusion and a final dose given interperitoneally after 8 hours. Survival at 6 days was 4/10 for the saline treated control group vs. 10/10 for the oxypurinol treated experimental group. Terminal blood urea nitrogen values of $190 \pm 34$ for the placebo-treated rats that died and morphologic examination of the kidneys confirmed that the 6 control rats died with renal failure. The mean blood urea nitrogen values for all placebo-treated rats vs. oxypurinol-treated rats were at $148 \pm 33$ vs. $73 \pm 29$, respectively (P < 0.05).

The foregoing studies, especially those demonstrating efficacy of post-resuscitative or post-ischemic therapy consisting essentially of IV administration of allopurinol, oxypurinol or deferoxamine constitutes a significant addition to the clinical armamentarium of medical practitioners, particularly those practicing in emergency departments and other clinical settings in which emergency treatment is required after an unexpected ischemic event.

We claim:

1. A method for treatment of a patient suffering an unanticipated condition of body tissue ischemia due to a stoppage of the inflow of arterial blood to said tissue to reduce tissue damage upon reperfusion of the tissue, said method consisting essentially of administering intravenously to said patient a therapeutically effective amount of a compound selected from the group consisting of effective amount of a compound selected from the group allopurinol, oxypurinol, and alkali metal salts of allopurinol and oxypurinol, the administration of said compound being initiated subsequent to the occurrence of the condition of body tissue ischemia and substantially simultaneously with resumption of blood flow to said tissues.

2. The method of claim 1 wherein the compound administered intravenously is allopurinol.

3. The method of claim 2 wherein the ischemic body tissue is heart muscle tissue.

4. The method of claim 3 wherein the patient is suffering from coronary thrombosis.

5. The method of claim 4 wherein the allopurinol is administered simultaneously with thrombolytic therapy.

6. The method of claim 1 wherein the ischemic body tissue is brain tissue.

7. The method of claim 2 wherein the patient is suffering from cardiac arrest and the compound is administered immediately subsequent to cardiopulmonary resuscitation.

8. The method of claim 1 wherein allopurinol is administered intravenously at a dosage of about 10 to about 50 milligrams per kilogram.

9. The method of claim 1 wherein the compound administered intravenously is oxypurinol.

10. The method of claim 9 wherein the ischemic body tissue is heart muscle tissue.

11. The method of claim 10 wherein the patient is suffering from coronary thrombosis.

12. The method of claim 11 wherein the allopurinol is administered simultaneously with thrombolytic therapy.

13. The method of claim 9 wherein the ischemic body tissue is brain tissue.

14. The method of claim 9 wherein the patient is suffering from cardiac arrest and the compound is administered immediately subsequent to cardiopulmonary resuscitation.

15. The method of claim 1 wherein oxypurinol is administered intravenously at a dosage of about 10 to about 50 milligrams per kilogram.

* * * * *

UNITED STATES PATENT AND TRADEMARK OFFICE
CERTIFICATE OF CORRECTION

PATENT NO. : 4,978,668

DATED : December 18, 1990

INVENTOR(S) : Charles F. Babbs et al.

It is certified that error appears in the above-identified patent and that said Letters Patent is hereby corrected as shown below:

In column 4, line 15, please replace "TO" with --OT--.

In column 5, line 18, please delete "effective amount of a compound selected from".

In column 5, line 19, please delete "the group".

Signed and Sealed this

Nineteenth Day of May, 1992

Attest:

DOUGLAS B. COMER

*Attesting Officer*        *Acting Commissioner of Patents and Trademarks*